United States Patent [19]
Rowe et al.

[11] Patent Number: 5,658,070
[45] Date of Patent: Aug. 19, 1997

[54] METHOD OF VARYING LUMINOUS INTENSITY OF LIGHT IN AN ILLUMINATION SYSTEM

[75] Inventors: T. Scott Rowe, Mission Viejo; Eric Marason; David Wilkinson, both of San Francisco, all of Calif.

[73] Assignee: Alcon Laboratories, Inc., Fort Worth, Tex.

[21] Appl. No.: 329,916

[22] Filed: Oct. 27, 1994

[51] Int. Cl.$^6$ .................................................. F21V 17/02
[52] U.S. Cl. ........................ 362/283; 362/284; 362/321; 362/324
[58] Field of Search ................. 362/32, 20, 321, 362/281, 280, 282, 283, 284, 293, 268, 804, 322, 324, 323; 600/178, 181; 606/4; 352/141; 353/88, 89, 91

[56] References Cited

U.S. PATENT DOCUMENTS

| | | |
|---|---|---|
| 3,016,800 | 1/1962 | Pliskin . |
| 3,775,606 | 11/1973 | Bazell et al. . |
| 4,061,911 | 12/1977 | Krasin . |
| 4,233,650 | 11/1980 | Hagner et al. . |
| 4,356,534 | 10/1982 | Hattori . |
| 4,397,523 | 8/1983 | Feinbloom et al. . |
| 4,425,599 | 1/1984 | Rieder et al. . |
| 4,439,024 | 3/1984 | Ito . |
| 4,608,622 | 8/1986 | Gonser . |
| 4,623,217 | 11/1986 | Hallén . |
| 4,628,416 | 12/1986 | Dewey . |
| 4,757,426 | 7/1988 | Scheller et al. . |
| 4,811,182 | 3/1989 | Solomon ............................ 362/321 |
| 5,053,934 | 10/1991 | Krebs ................................. 362/321 |
| 5,217,285 | 6/1993 | Sopori . |
| 5,281,984 | 1/1994 | Burton et al. . |
| 5,382,987 | 1/1995 | Sperling ............................ 351/206 |
| 5,510,969 | 4/1996 | Rodger et al. ................... 362/321 |

FOREIGN PATENT DOCUMENTS

| | | |
|---|---|---|
| 0611547 | 8/1994 | European Pat. Off. . |
| 5232387 | 10/1993 | Japan . |
| WO 92/11548 | 7/1992 | WIPO . |

OTHER PUBLICATIONS

Grieshaber & Co., Inc., "G.L.S. The Grieshaber Light Source" brochure, 1990.

*Primary Examiner*—Stephen F. Husar
*Assistant Examiner*—Thomas M. Sember
*Attorney, Agent, or Firm*—Jeffrey S. Schira

[57] ABSTRACT

A fiberoptic illumination system having an attenuator with a "multiple wedge" aperture that more uniformly attenuates the light beam striking the fiberoptic without changing the color temperature of the light beam or affecting the exit divergence angle of the light beam. The system includes an optical housing design having orthogonal lights paths that allows two fiberoptics to be illuminated from the same bulb, two bulbs located in primary and back-up positions, respectively, mounted on a rotating carousel and a retinal protection filter that filters out wavelengths of light harmful to the retina.

1 Claim, 8 Drawing Sheets

METHOD OF VARYING LUMINOUS INTENSITY OF LIGHT IN AN ILLUMINATION SYSTEM

BACKGROUND OF THE INVENTION

The present invention relates to fiberoptic illumination systems and more particularly to fiberoptic illumination systems used in ophthalmic surgery.

Fiberoptic illumination systems are widely used in the medical field for illuminating body cavities, particularly during endoscopic (small incision) surgery. These devices generally include some means for attenuating the luminous density or light-flux of the light beam.

For example, the luminous density or light-flux from the light source can be controlled by varying the feeding current or voltage to the light source. This method of attenuating the light source will change the color temperature of the light and thus the color of the object illuminated. Various attenuating filters may also be used, but attenuating filters can reduce maximum illumination of the cavity. Optical diaphragms such as an iris diaphragm will change the entrance and exit angles of the light beam into and out of the optic fiber. Sectored or fan-fading diaphragms, such as those disclosed in U.S. Pat. No. 4,233,650, reduce the maximum illumination of the cavity. Wedge-shaped shutters, such as those disclosed in U.S. Pat. Nos. 3,106,800 and 4,425,599, do not substantially reduce the maximum amount of illumination in the cavity; however, these types of shutters preferentially attenuate the outer ("cooler") portion of the light beam, and do not commensurably attenuate the inner ("hotter") part of the beam, thus resulting in a hotter light beam (change in color temperature) exiting the fiberoptic. In addition, attenuating only the outer portion of the beam results in non-optimal illumination of the numerical aperture of the fiber and poorer light mixing in the fiber.

One prior art device sold by Grieshaber & Company, Inc., includes an ultraviolet (UV) filter; however, the UV spectrum of the lamps used in this and other illumination systems generally is considered to extend from 200 nanometers (nm) to 400 nm, and wavelengths longer than 400 nm have been shown to be injurious to the retina.

Accordingly, a need continues to exist for a fiberoptic illumination system that allows for the uniform attenuation of the amount of light reaching the fiberoptic without changing the color temperature or entrance angle of the light or reducing the maximum amount of light reaching the object to be illuminated. A need also continues to exist for a fiberoptic illumination system that attenuates the wavelengths of light shown to be injurious to the retina.

BRIEF DESCRIPTION OF THE INVENTION

The present invention improves upon prior art illumination systems by providing a system having an attenuator with a "multiple wedge" aperture that more uniformly attenuate the light beam striking the fiberoptic without changing the color temperature of the light beam or affecting the entrance angle of the light beam. In addition, the present system uses a novel, compact optical housing design with orthogonal light paths that allow two fiberoptics to be illuminated from the same bulb. The present system also mounts two bulbs in the primary and back-up positions on a unique carousel that automates bulb replacement in the event of bulb failure in the primary position, an important feature if bulb failure occurs during surgery. The present system may also include a retinal protection filter for use during ophthalmic surgery that reduces certain harmful wavelengths of light from reaching the retina, thus extending the duration of retinal illumination during ophthalmic surgery.

Accordingly, one objective of the present invention is to provide an illumination system that uniformly attenuates the light beam striking the fiberoptic.

Another objective of the present invention is to provide an illumination system that attenuates the light beam striking the fiberoptic without changing the color temperature of the output beam.

Still another objective of the present invention is to provide an illumination system that attenuates the light beam striking the fiberoptic without changing the maximum entrance angle of the beam.

Still another objective of the present invention is to provide an illumination system with an attenuator with a "multiple wedge" aperture.

Still another objective of the present invention is to provide an illumination system with both bulbs oriented in the primary and back-up bulb positions mounted on a rotating carousel.

Stir another objective of the present invention is to provide an illumination system with a retina/protection filter.

Still another objective of the present invention is to provide an illumination system with dual light paths.

These and other objectives and advantages of the present invention will become apparent from the drawings, detailed description and claims which follow.

DETAILED DESCRIPTION OF THE INVENTION

Figure 1:
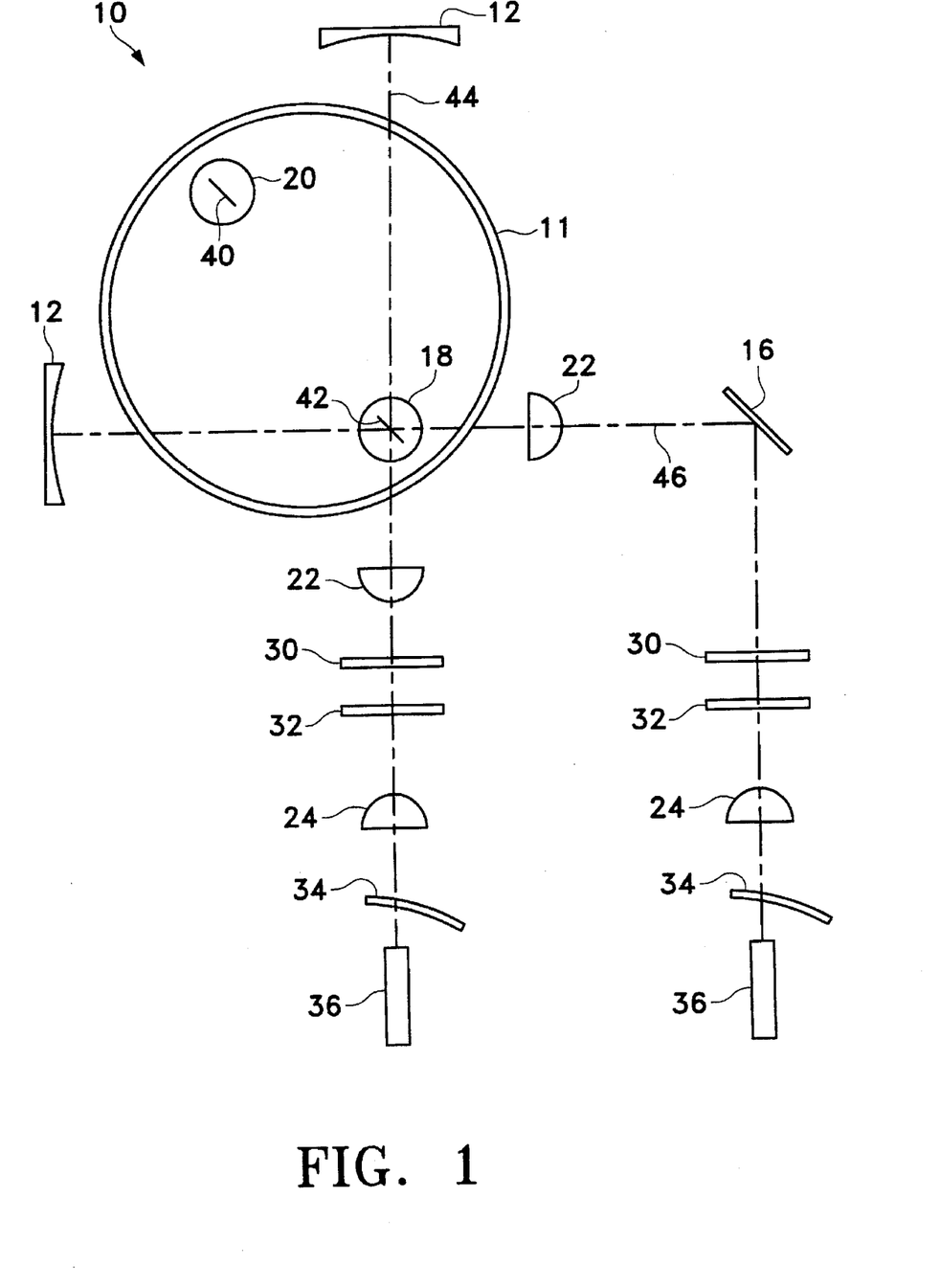
FIG. 1 is a schematic illustration of the illumination system of the present invention.
Figure 2:
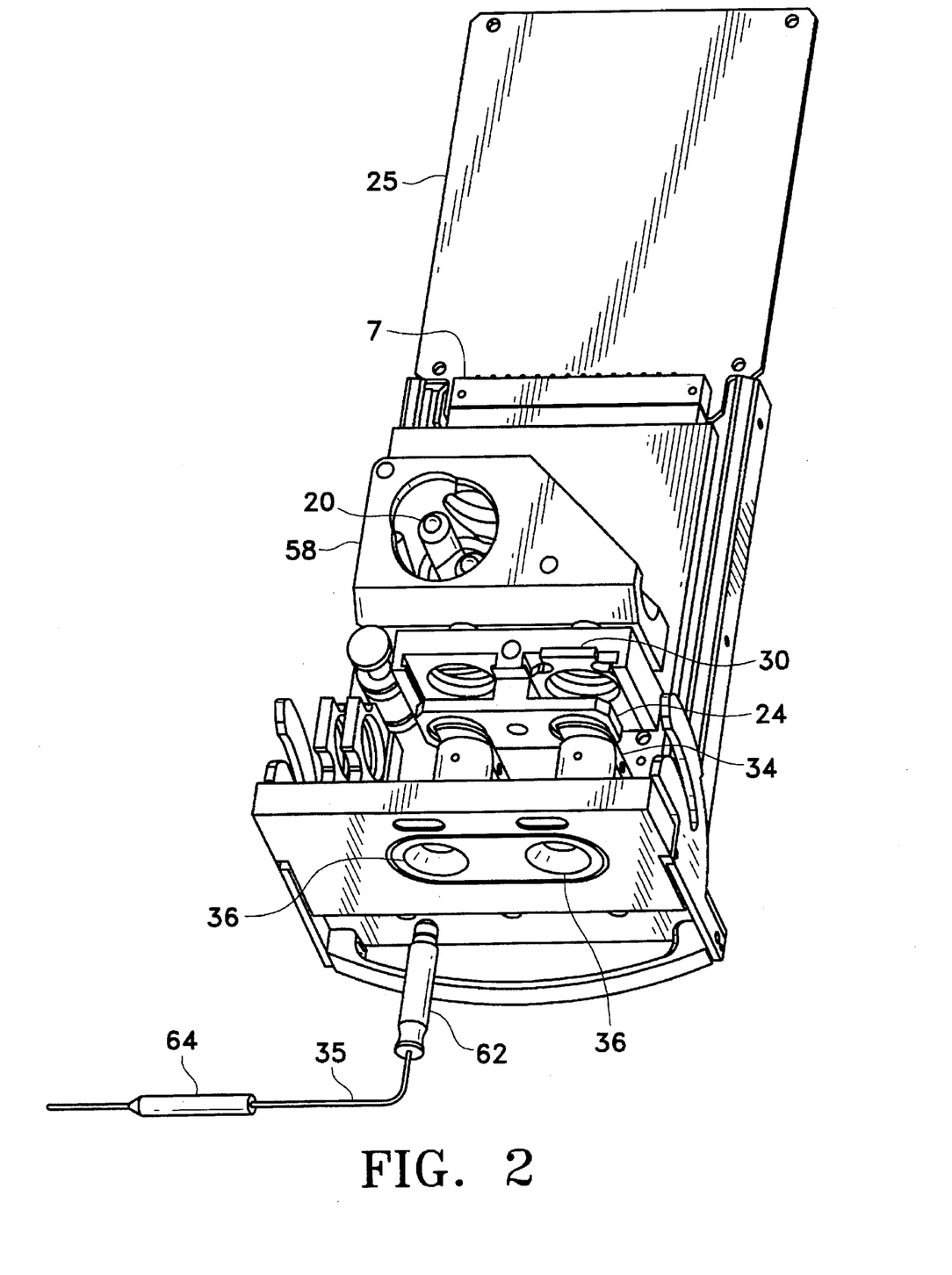
FIG. 2 is a top perspective view of one embodiment of the illumination system of the present invention.
Figure 3:
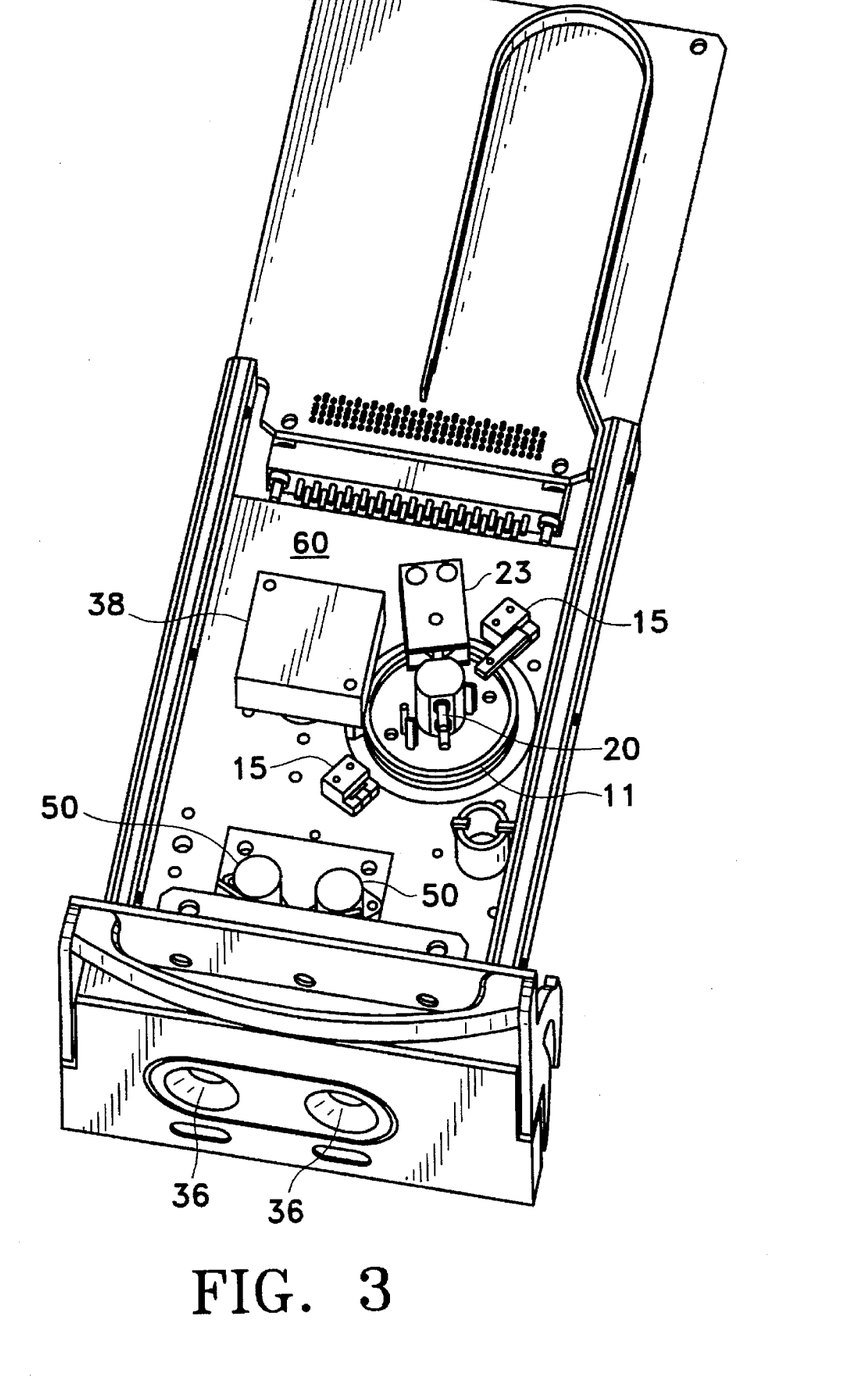
FIG. 3 is a bottom perspective view of the illumination system of the present invention illustrated in FIG. 2.
Figure 4:
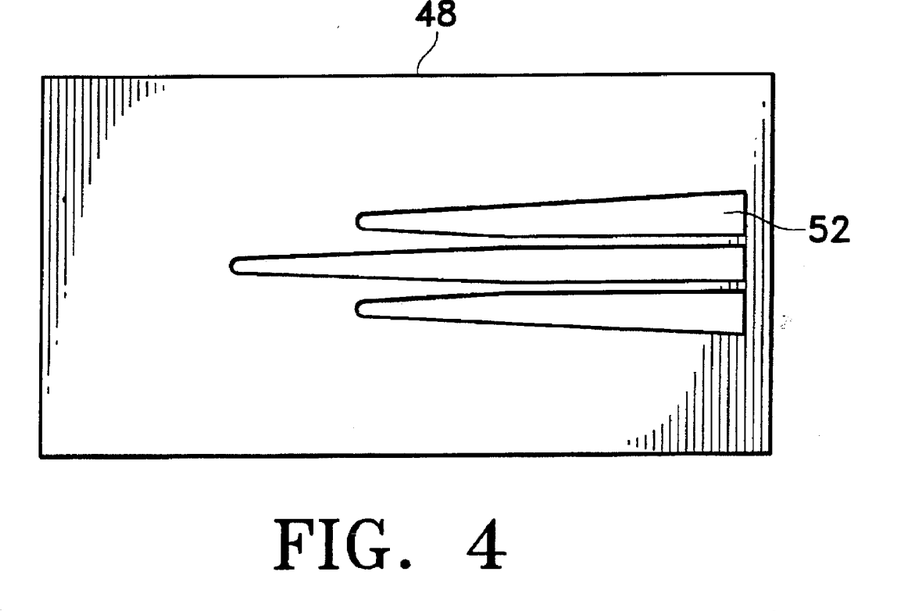
FIG. 4 is an elevational view of one embodiment of the attenuator that may be used in the illumination system of the present invention.
Figure 5:
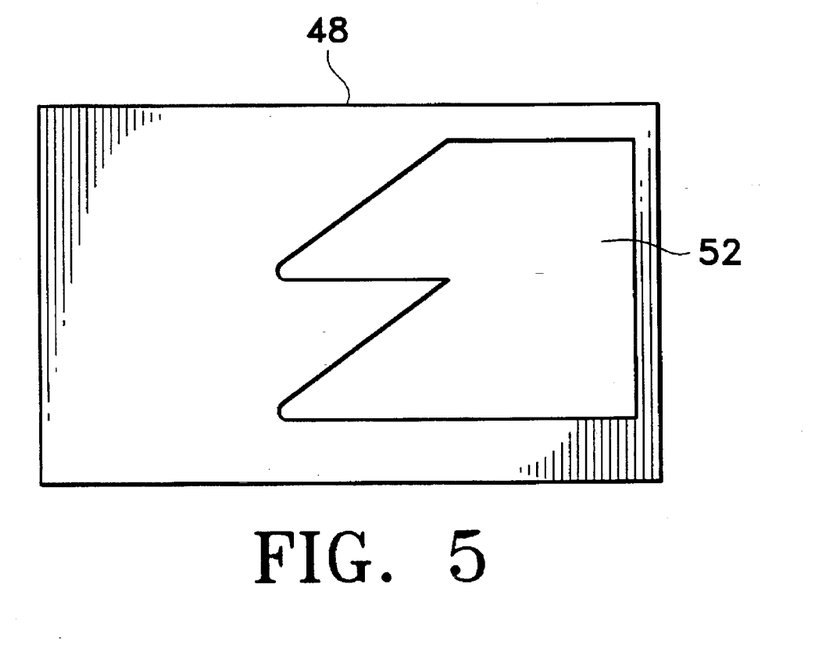
FIG. 5 is an elevational view of a second embodiment of the attenuator that may be used in the illumination system of the present invention.
Figure 6:
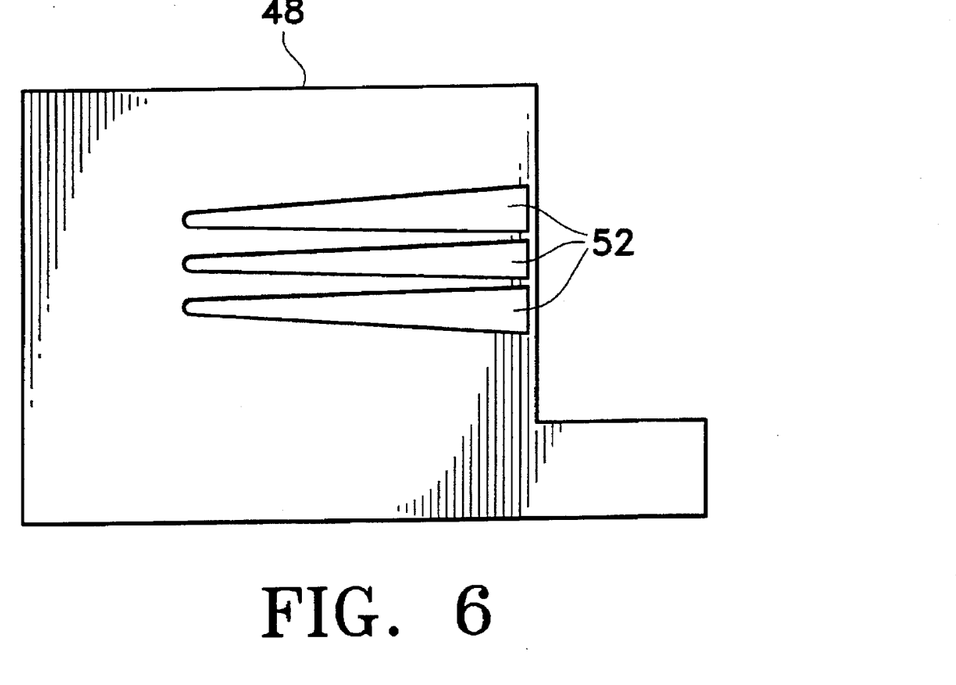
FIG. 6 is an elevational view of a third embodiment of the attenuator that may be used in the illumination system of the present invention.
Figure 7:
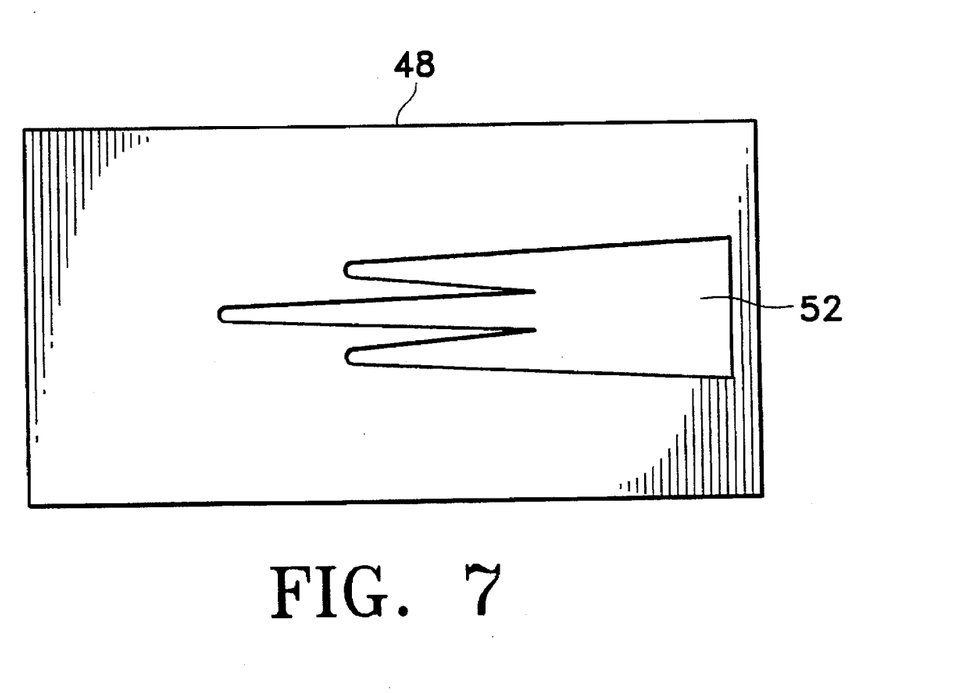
FIG. 7 is an elevational view of a fourth embodiment of the attenuator that may be used in the illumination system of the present invention.
Figure 8A:
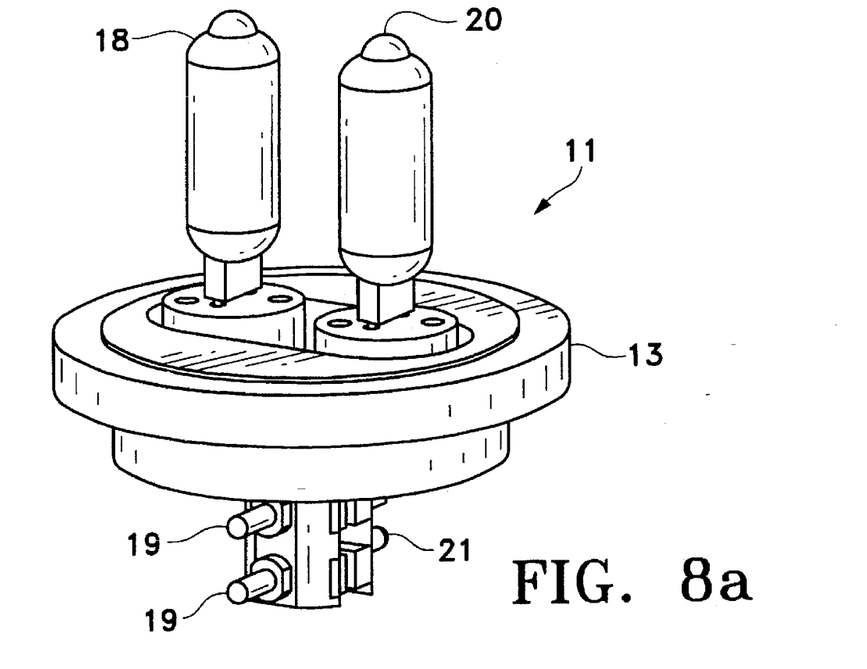
FIGS. 8a and 8b are enlarged perspective views of the carousel that may be used in the present invention.
Figure 8B:
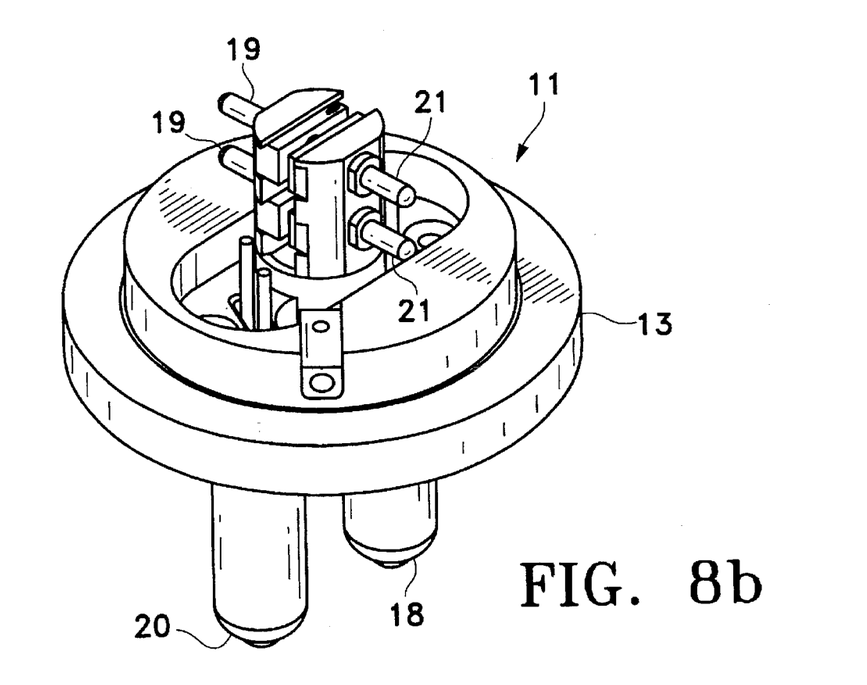

As can be seen in FIGS. 1, 2 and 3, illumination system 10 generally consists of carousel 11, spherical mirrors 12 and 16, bulbs 18 and 20, lenses 22 and 24, retinal protection filters 30, infrared (IR) filters 32, attenuators 34 and fiberoptic connectors 36. Power is provided to system 10 by an outside source (not shown) through connector 7.

Figure 9:
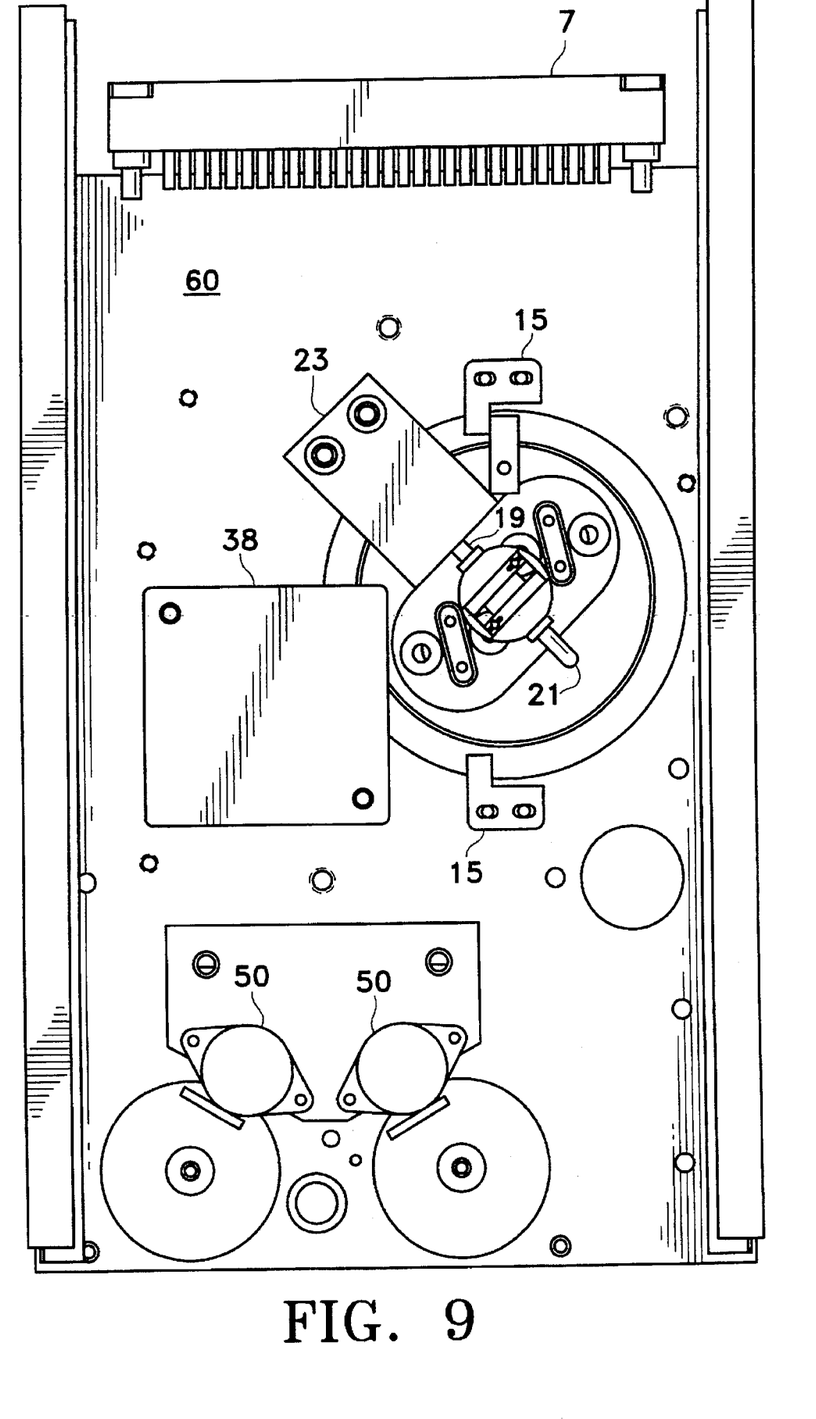
FIG. 9 is an enlarged bottom plan view of the illumination system of the present invention illustrated in FIG. 3.

Carousel 11 is round, approximately 2 inches in diameter and, as best seen in FIGS. 3 and 9, rotated by stepper motor 38. Suitable stepper motors 38 are commercially available from sources such as Seiko Corporation. Bulbs 18 and 20 are mounted on the top side of carousel 11 (the side opposite of stepper motor 38) so that filaments 40 and 42 are at an angle of approximately 45° with respect to primary optical axis 44 and secondary optical axis 46 when bulbs 18 and 20 are in the primary operating position (as illustrated by bulb 18 in FIG. 1). This 45° bulb orientation induces a more substantial depth of field, allowing for looser tolerances and fewer mechanical adjustments. Bulbs 18 and 20 may be any electric bulb suitable for use in a fiberoptic illumination system but ANSI standard BRL type (tungsten-halogen) bulbs are preferred.

Figure 10:
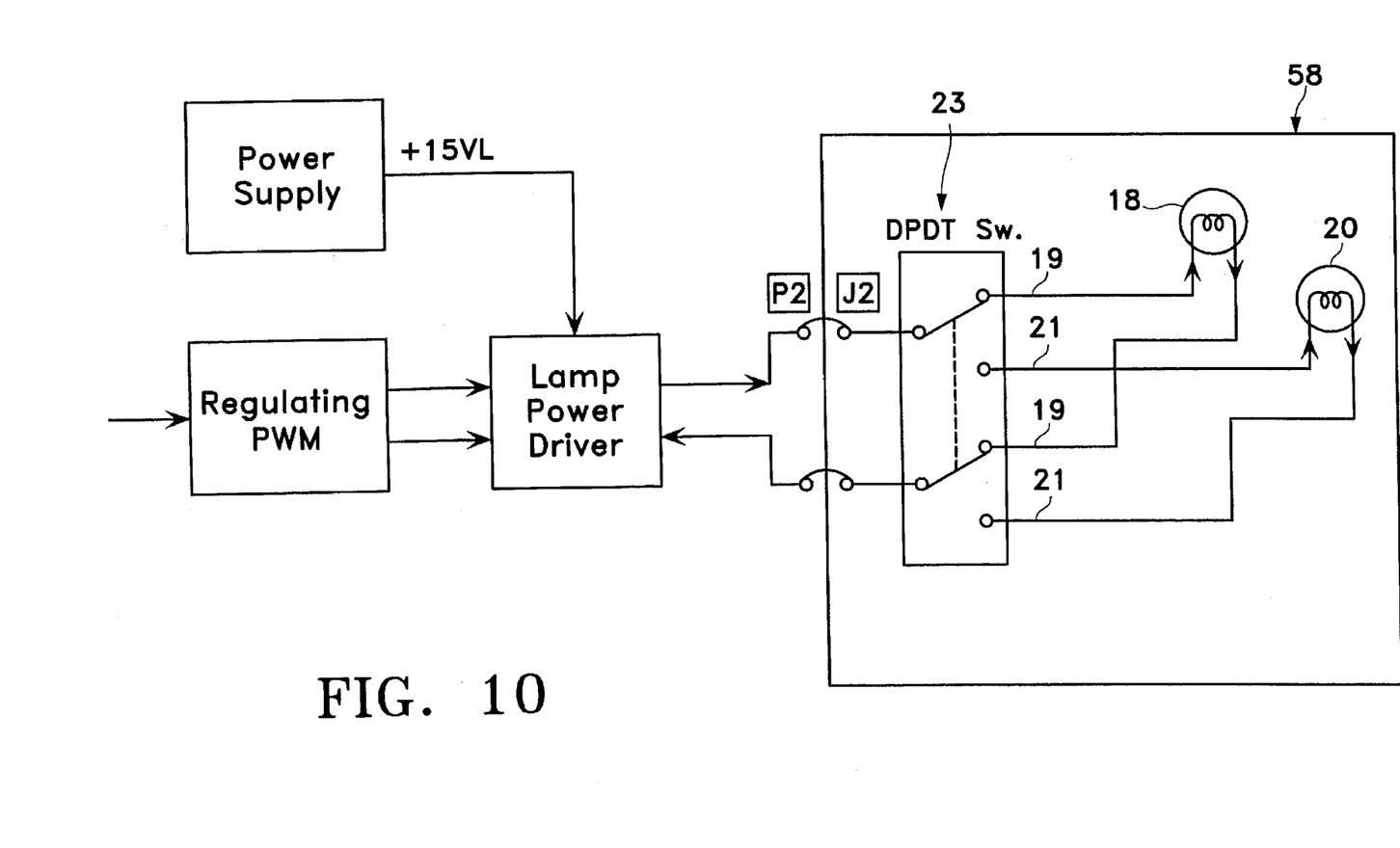
FIG. 10 is a block diagram of the bulb power circuit that may be used in the present invention.

As best seen in FIGS. 8a, 8b, 9 and 10, carousel 11 is mounted on precision ring bearing 13 that registers carousel 11 to optics plate 60 allowing carousel 11 to be rotated by stepper motor 38, preferably using a smooth friction drive. The position of carousel 11 is tracked using two Hall effect type endpoint detectors 15. Power to bulbs 18 and 20 is provided by pins 19 and 21, respectively, through power connector 23. When carousel 11 is automatically rotated by stepper motor 38 in response a signal generated by controller board 25 resulting from a sensed bulb failure, one pair of pins 19 or 21 engages power connector 23, thereby providing power to bulb 18 or 20 in the primary position, as best seen in FIG. 10.

As can be seen in FIGS. 1 and 2, optical housing 58 encloses carousel 11, bulbs 18 and 20, lenses 22 and mirrors 12 and 16. Housing 58 may be made from aluminum alloy, chemically anodized on the outside with a flat black exterior. As can best be seen in FIG. 1, light paths 44 and 46 are perpendicular to each other. This orthogonal layout of light paths 44 and 46 maximizes the collection of photons from bulb 18 and allows for dual fiberoptic connectors 36 in a relatively compact design. Spherical mirrors 12 collect photons that might otherwise be lost and redirects the photons back through bulb 18 to be collimated by aspheric condensing lenses 22. By maximizing the collection of photons, a lower power dissipation bulb may be selected, thereby increasing the electrical to optical efficiency of system 10. Mirrors 12 are preferably first surface spherical reflectors and commercially available from sources such as Edmund Scientific. Mirror 16 is preferably an elliptical flat first surface high reflector mirror and commercially available from sources such as Edmund Scientific. Lenses 22 and 24 are preferably aspheric condenser elements and commercially available from sources such as Melles Griot, Irvine, Calif.

As can best be seen in FIG. 2, system 10 also includes retinal protection filters 30 and IR filters 32. Retinal protection filters 30 are multi-layer interference dielectric coatings on a glass substrate and filter out over 95% of the light between approximately 325 nm and 450 nm, extending outside the ultraviolet wavelengths but roughly the absorption bands of the photochemicals opsin, retinal and xanthophyll, and the wavelength range believed to be most injurious to the retina, but allow over 90% of the light between approximately 460 nm and 700 nm to pass. IR filters 32 filter out approximately 95% of the light from 700 nm to 1100 nm, thus, helping to eliminate heat from the light in light paths 44 and IR filters are commercially available from sources such as QSP Optical Technologies, Santa Aria, Calif. Retinal protection filters 30 are approximately 28 mm in diameter, approximately 2 mm thick and are commercially available from sources such as QSP Optical Technologies, Santa Aria, Calif. Alternatively, the retinal protection and IR filtering aspects of filters 30 and 32, respectively, can be combined in one dual purpose filter (not shown).

Aspheric lenses 24 focus the light traveling along light paths 44 and 46 through attenuators 34 and onto fiberoptics 35 in fiberoptic connectors 36 designed to match an industry standard ACMI connector 62 attached to probe 64. Connectors 36 have a receptacle 37 with a spring loaded ball plunger (not shown) designed to pre-load the aperture of connector 62 against a precision located surface positioned at the foci of lenses 24. The f/number of lenses 24 is matched to the numeric aperture of fiberoptic 35 within connectors 62 so that the cone of light entering fiberoptic 35 approaches, but does not exceed, the critical angle of total internal reflection within the fiber. Connectors 36 and fiberoptics 35 are commercially available from sources such as Infinitec, St. Louis, Mo.

As best seen in FIGS. 3–7, attenuators 34 contain shutters 48 rotated by stepper motors 50. Shutters 48 contain apertures 52 of a "multiple wedge" design. This design allows for a more uniform mixing of light within the multi-mode, step-index fiberoptic by variably, according to the angle of shutters 48, blocking portions of the central and exterior focused beam, thereby providing more uniform illumination of the target surface. Such a design also removes portions of both the less intense light on the outer edge of the light beam, and the more intense light in the central part of the beam, thereby attenuating the amount of light reaching connectors 36 without changing the color temperature of the beam. Shutters 48 preferably are made from soft brass or aluminum alloy, chemically anodized by processes well known in the art, and bent on a radius, for example, 0.79 inches.

System 10 is designed so that no opto-mechanical adjustments are necessary. All optical elements are mounted either to optical housing 58 or plate 60 using registration pins (not shown) fitted to precision bores using suitable adhesives or, preferably, screw fasteners.

This description is given for purposes of illustration and explanation. It will be apparent to those skilled in the relevant art that changes and modifications may be made to the invention described above without departing from its scope or spirit.

We claim:

1. A method of varying luminous intensity of light in an illumination system, comprising the steps of:
    a) collecting light having a color temperature and a divergence angle emitted by a bulb and directing the light along a light path;
    b) directing the light in the light path through an attenuator that is bent on a radius, the attenuator having an aperture of a multiple wedge design; and
    c) attenuating the luminous intensity of the light without modifying the color temperature or the divergence angle of the light by rotating the attenuator with a motor.

* * * * *